US008056400B2

United States Patent
Reintjes et al.

(10) Patent No.: US 8,056,400 B2
(45) Date of Patent: Nov. 15, 2011

(54) METHOD AND APPARATUS FOR FLUID SAMPLING

(75) Inventors: John F. Reintjes, Alexandria, VA (US); John E. Tucker, Centreville, VA (US); Lawrence L. Tankersley, Annapolis, MD (US); Paul L. Howard, New Market, NH (US)

(73) Assignee: United States of America as represented by the Secretary of the Navy, Washington, DC (US)

( * ) Notice: Subject to any disclaimer, the term of this patent is extended or adjusted under 35 U.S.C. 154(b) by 617 days.

(21) Appl. No.: 12/206,139

(22) Filed: Sep. 8, 2008

(65) Prior Publication Data

US 2009/0211379 A1    Aug. 27, 2009

Related U.S. Application Data

(60) Provisional application No. 61/031,390, filed on Feb. 26, 2008.

(51) Int. Cl.
| G01N 1/14 | (2006.01) |
| G01N 1/20 | (2006.01) |
| G01N 21/85 | (2006.01) |

(52) U.S. Cl. .............. 73/64.56; 73/863.23; 73/863.83; 73/863.84

(58) Field of Classification Search ............ 73/64.56, 73/168, 863.23, 863.83–863.84, 863.86, 73/864.34–864.35; 250/576
See application file for complete search history.

(56) References Cited

U.S. PATENT DOCUMENTS

| 3,390,580 | A | * | 7/1968 | Taylor ................. 73/864.34 |
| 3,912,127 | A | | 10/1975 | Georgi |
| 4,900,683 | A | * | 2/1990 | Metzger et al. ............. 436/179 |
| 4,924,695 | A | * | 5/1990 | Kolpak ................. 73/19.01 |
| 5,010,829 | A | * | 4/1991 | Kulkarni ................. 110/346 |
| 5,572,320 | A | | 11/1996 | Reintjes et al. |
| 5,619,333 | A | | 4/1997 | Staff et al. |
| 5,834,656 | A | * | 11/1998 | Seltzer ................. 73/863.71 |
| 5,894,083 | A | * | 4/1999 | Hiraoka et al. ............. 73/23.2 |
| 6,049,381 | A | | 4/2000 | Reintjes et al. |
| 6,058,773 | A | | 5/2000 | Zimmerman et al. |
| 6,637,277 | B2 | | 10/2003 | Gamache et al. |
| 7,921,739 | B2 | * | 4/2011 | Fjerdingstad et al. ... 73/64.56 X |
| 2005/0051329 | A1 | | 3/2005 | Blaisdell |
| 2006/0070426 | A1 | | 4/2006 | Pelletier |
| 2006/0196254 | A1 | | 9/2006 | Fjerdingstad et al. |
| 2010/0002234 | A1 | * | 1/2010 | Cormier et al. ............. 356/436 |

FOREIGN PATENT DOCUMENTS

| JP | 04301743 A | * | 10/1992 |
| SU | 443276 A | * | 12/1974 |
| WO | WO 2004038281 A1 | * | 5/2004 |

* cited by examiner

*Primary Examiner* — Thomas P Noland
(74) *Attorney, Agent, or Firm* — Amy L. Ressing; Sally A. Ferrett

(57) ABSTRACT

A method and system for particle entrained fluid sampling, capable of sampling a high pressure and/or high flow rate fluid flow system using a pressure intensifier for applying pressure or suction to the fluid sample in the fluid sampling system operatively connected to a sample extractor and a sample analysis device. The pressure intensifier for applying pressure or suction is adjustable to provide control over the sample flow in the fluid sampling system. The fluid sampling system of the present invention may be particularly applicable to monitoring the condition of hydraulic and lubrication systems.

17 Claims, 8 Drawing Sheets

METHOD AND APPARATUS FOR FLUID SAMPLING

CROSS REFERENCE TO RELATED APPLICATIONS

This application is a non-provisional of provisional application 61/031,390 under 35 USC 119(e), filed on Feb. 26, 2008, the entire disclosure of which is incorporated by reference herein.

BACKGROUND OF THE INVENTION

1. Field of the Invention

The present invention relates to a novel method and system with an optional purging means for sampling fluids with entrained particles. The system is particularly applicable for monitoring particulate contamination of fluid samples using optical analysis for purposes of monitoring the condition and wear of machinery and monitoring operational parameters.

2. Description of the Related Technology

There exist a number of particulate fluid sampling systems and methods that may be operated in conjunction with an optical sensor. These systems and methods are used for a variety of different applications. Particulate monitoring is particularly important to monitoring and maintenance of machinery, especially where functional fluids are employed. For example, the analysis of debris particles in lubricating oil is a well-known method of monitoring the condition of oil wetted machinery. Particulate monitoring is also an essential maintenance procedure for hydraulic systems.

Particle fluid sampling systems may generally be categorized as either manual sampling systems and online analyzer systems. Traditionally, particulate monitoring involved manually withdrawing a sample of particle entrained fluid and transporting it to a laboratory for analysis. After reaching the laboratory, the samples had to be prepared for microscopic analysis using conventional methods such as centrifugal separation, separation onto a filter patch and ferrography. Only then was it possible to evaluate the level of particulate contamination by performing tests such as particle counting and microscopic analysis of debris particles. An expert then examined the particulates and the machine condition at the time the sample was taken is subjectively evaluated.

Unfortunately, this procedure is inefficient, time consuming, expensive and has limited effectiveness. Among the deficiencies of this conventional fluid sampling method are the long delays between sample extraction and obtaining an analysis of the sample, the necessity of sample preparation, inaccuracies resulting from subjective evaluation of samples and the fact that sampling often provides non-representative samples of the fluid since such samples are generally taken from drain ports or sumps. Additionally, the mere fact that the sample must be manually extracted substantially contributes to the inefficiency and expense of the process.

Online analyzer systems, such as online oil debris analyzers, by contrast, allow for sample analysis without requiring the manual extraction of a sample. Most of the online debris monitors, however, function to detect magnetic or ferromagnetic particles by using inductive, eddy current or magnetic interactions and provide only limited information about the debris particles. While systems such as the LaserNet Fines online optical debris monitor, described in U.S. Pat. No. 5,572,320, may be more robust and provide more data analysis, these online systems are similar in that they cannot be used to analyze non-magnetic or non-ferromagnetic particles.

U.S. Pat. No. 5,619,333 is another example of an online analyzer. It discloses a sampling apparatus, an optical analysis means and a method for monitoring particulate contamination of hydraulic fluids which may be employed to sample a high pressure stream of fluid. The apparatus includes an optical analysis means and a double acting piston for extracting particle entrained fluid samples. The fluid sampling system includes two connections to the hydraulic fluid apparatus, one on either side of the double-acting piston, such that samples can be drawn from either connection and fluid pressure of an incoming sample can be employed to equalize pressure applied to a sample on the other side of the double-action piston which is being returned to the hydraulic system. As a result, system pressure is inconsequential to operation since the fluid sampling system acts with controlled low differential pressure on both sides of the piston. This piston driven fluid sampling system, however, is limited by a fixed flow rate and flow volume and is therefore incapable of adapting to the requirements of different optical sensors and different fluid flow systems, thereby requiring a custom design for each fluid system. For this reason, it is also inefficient in extracting and expelling fluid samples. Moreover, the disclosed system does not include purging lines for cleaning the sample extraction system.

U.S. Patent application publication no. US 2006/0070426 A1 discloses another optical online analyzer adapted for field analysis at high temperatures and pressures. The system includes a sample manifold and a pressure intensifier, such as a piston, for withdrawing samples from a high pressure system.

Fluid sampling systems are also typically incapable of regulating pressures so as to adjust to different fluid flow systems. Furthermore many fluid sampling systems are incapable of operating in high pressure fluid flow systems, and thus are limited to analyzing low pressure fluid flow systems or a low pressure portion of a fluid flow system, samples of which may not be representative of the overall system condition.

Therefore, there exists a need to provide a system and method for sampling and/or purging fluids with entrained particles that offers flexibility in working with different types of optical sensors and different fluid flow systems. There also exists a need to develop a system capable of regulating fluid flow pressure which enables online analysis of both magnetic/ferromagnetic and non-magnetic/ferromagnetic particles.

SUMMARY OF THE INVENTION

In one aspect, the present invention is directed to an automated fluid sampling system capable of sampling a fluid flow system having a pressure of from about 20 psi to about 3500 psi. The system comprises a sample extractor, apparatus for applying pressure or suction to a fluid sample in the fluid sampling system and at least one sample analysis device. The fluid sampling system is capable of adjustably regulating suction applied to extract fluid samples, as well as pressure applied to return fluid samples to the fluid flow system.

A second aspect of the invention is directed to a fluid sampling system comprising at least two fluid flow circuits capable of fluid purging as well as sampling a fluid flow system. Each fluid flow circuit comprises sample extractor, apparatus for applying pressure or suction to a fluid sample in the fluid sampling system and at least one sample analysis device. This embodiment of the fluid sampling system is capable of purging the sampling system, adjustably regulating suction applied to extract fluid samples, as well as pressure applied to return fluid samples to the fluid flow system.

A third aspect of the present invention is directed to a method for fluid sampling comprising the steps of providing a fluid sampling system, extracting a sample from a fluid flow using apparatus to adjustably regulate sample extraction, analyzing the sample and returning the sample to said fluid flow system.

DETAILED DESCRIPTION OF THE PREFERRED EMBODIMENTS

For illustrative purposes, the principles of the present invention are described by referencing various exemplary embodiments thereof. Although certain embodiments of the invention are specifically described herein, one of ordinary skill in the art will readily recognize that the same principles are equally applicable to, and can be employed in other compositions and methods. Before explaining the disclosed embodiments of the present invention in detail, it is to be understood that the invention is not limited in its application to the details of any particular embodiment shown. The terminology used herein is for the purpose of description and not of limitation. Further, although certain methods are described with reference to certain steps that are presented herein in certain order, in many instances, these steps may be performed in any order as may be appreciated by one skilled in the art, and the methods are not limited to the particular arrangement of steps disclosed herein.

The present invention is directed to a particle entrained fluid sampling systems and methods for their use. In one embodiment, the fluid sampling system includes a piston and two check valves which cooperate to sample fluid from a fluid flow system. The sampling system of the present invention is capable of sampling from a hydraulic or lubrication system operating at high pressures and/or high flow rates. It is further capable of optimizing the process of sample extraction, analysis and return of the sample to the fluid flow system.

Figure 1:
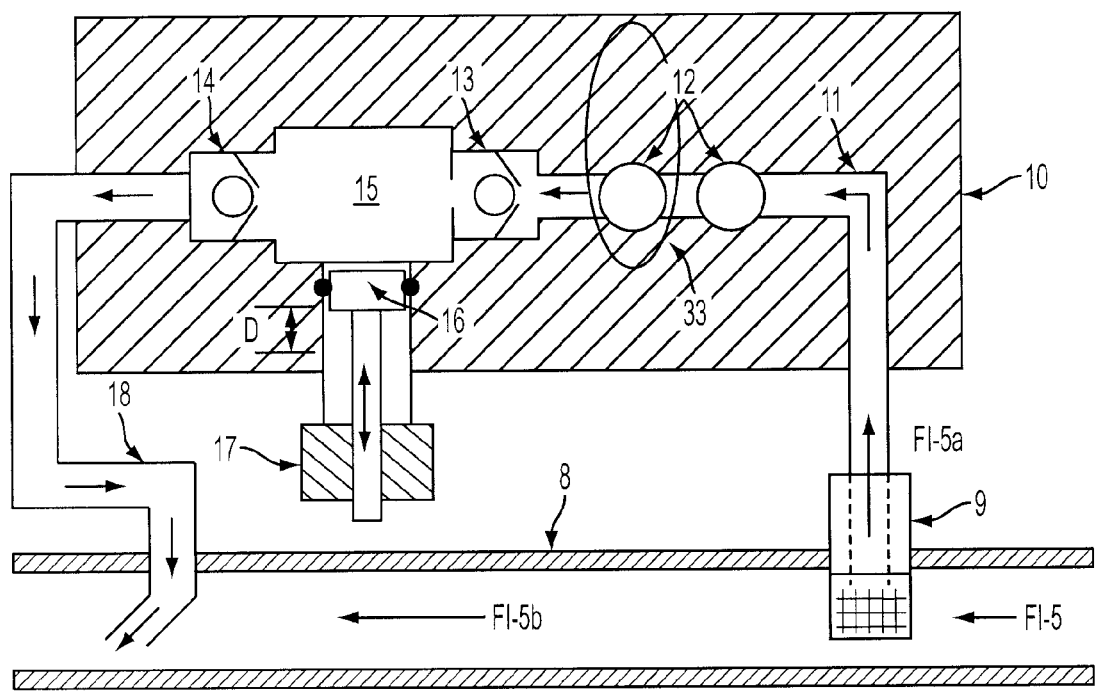
FIG. 1 is a schematic diagram of one embodiment of a fluid sampling system of the present invention including a single flow circuit.

The fluid sampling system of the present invention may include multiple flow circuits for sampling and purging of the system. In one embodiment, the fluid sampling system includes only a single fluid flow circuit that enables extraction, optical analysis and return of a particle entrained sample from a fluid flow. As shown in FIG. 1, the fluid flow circuit of the sampling system includes a sample extractor 9 connected to the fluid flow F1-5 in flow tube 8. Within sample extractor 9, there is an inlet particle size separator means, such as a screen, which controls the size range of particles sampled to allow the particle analysis to concentrate on a size range of interest, for example particles that would indicate moderate contamination or early failure development. In the fluid sampling system, the sampled fluid flows from sample extractor 9 via a sample conduit 11 past viewing ports 12 to a first spring-loaded ball check valve 13. Fluid may flow through first ball valve 13 into a chamber 15 and then through a second spring-loaded ball check valve 14 into a fluid return conduit 18 whereby the fluid sample may be returned to flow tube 8. A reciprocating piston 16 may be employed to exert suction or pressure on fluid located in chamber 15 and thereby actuate first and second spring-loaded ball valves 13, 14. A suitable actuator 17 is provided to move piston 16 up and down as shown in FIG. 1.

Fluid sample F1-5a may be extracted into and moved along the first fluid flow circuit by any conventional means, such as suction applied by piston 16 or by the pressure of fluid in flow tube 8. As shown in FIG. 1, flow sample F1-5a is extracted by suction via sample extractor 9. As a result of suction applied by piston 16, ball valve 13 is opened, as shown in FIG. 1, and fluid sample F1-5a is further drawn past viewing ports 12 and into chamber 15. Suction is induced by a pressure differential between the first fluid flow circuit and the pressure in tube 8. The suction may be regulated by the combined action of reciprocating piston 16 being drawn down by actuator 17, which is operably connected to the first fluid flow circuit system, and check valves 13 and 14. Piston 16 and/or actuator 17 may be controlled in any suitable manner. One control method involves wireless control from a remote location. Actuator 17 may be driven by any conventional means capable of controlling the stroke and velocity of piston 16. In a preferred embodiment, actuator 17 is operated by a cam, preferably a motor driven cam arrangement, or spring and damper mechanism.

Piston 16 may be any suitable pressure intensifier. A pressure intensifier is a device which acts to regulate or apply pressure to a sample and/or regulate or apply suction to a sample. Any suitable, conventional apparatus for regulating or applying pressure or suction may be employed as a pressure intensifier in accordance with the present invention, though pressure intensifiers such as actuated pistons are preferred due to their ability to adjust the amount of pressure or suction applied by such devices.

A subsequent downward motion of piston 16 in FIG. 1, opens check valve 13 and closes check valve 14. This induces a pressure drop within chamber 15 in comparison to the pressure in tube 8 and the spring of check valve 13, which induces fluid flow sample F1-5a to travel from tube 8 to chamber 15. Fluid flow may then be regulated by controlling the degree of the pressure drop. The preload on these check valves determines the inlet and exit cutoff pressures of these valves. Suitable valves 13, 14 may be selected to adjust and customize these cutoff pressures in order to meet or exceed the requirements of a particular fluid flow system. In one embodiment, the check valves 13 and 14 may be spring-loaded check valves or ball valves. Other suitable, conventional valves may also be employed within the scope of the invention. When piston 16 reaches the bottom of its stroke and no longer applies suction since the downward movement of piston 16 has ceased, the spring or ball of check valve 13 closes the valve 13. Piston 16 and check valve 13 work together to regulate transport of fluid sample F1-5a from tube 8 to chamber 15. For example, the apparatus may regulate, and if necessary, supply a sufficient force to draw fluid sample F1-5a through tube 8 to chamber 15 at a uniform flow rate or at a particular, desired flow rate. The length of the piston stroke or the size of the piston 16 may be varied in a conventional manner to adjust the quantity of sample to be extracted, if desired, though for most systems this will not be necessary.

Piston 16 may be drawn downward at any suitable rate which enables operation of the sample analysis device. Piston 16 may be actuated by any suitable means such as pressure in inlet tube 11, a motor driven cam that permits the piston to be driven by the inlet pressure at a desired rate, or other means that allow the piston to retract in a controlled manner. In a preferred embodiment, the piston velocity is set to optimize the extraction of fluid sample F1-5a, to enable sample analysis by controlling the sample flow rate past viewing ports 12, and to cooperate with sample analysis device 33. Preferably, a drop in pressure is induced by a combination of piston 16 and check valve 13, wherein the induced pressure is significantly less than the pressure in tube 8 so as to enable flow of fluid sample F1-5 into chamber 15. In an exemplary embodiment, the pressure is preferably about ½ to about 2 times less than the pressure in tube 8, more preferably, about ½ to about 1½ times less than the pressure in tube 8 and most preferably, about 1 to about 1½ times less than the pressure in tube 8.

As shown in FIG. 1, prior to entering chamber 15, fluid sample F1-5a passes one or more viewing ports 12 for analysis. The amount and the flow rate of fluid sample F1-5a that is drawn past viewing ports 12 can be varied and is controlled by the downward stroke of piston 16. This permits the sampling device of the present invention to be used in conjunction with a variety of different fluid flow systems and/or fluid analysis devices 33. In a preferred embodiment, the amount and flow rate of the fluid sample is suitable to enable fluid analysis, particle analysis and/or is compatible with the operation of a sample analysis device 33. Viewing ports 12 are operably associated with sample analysis device 33 which is capable of detecting at least one characteristic of sample fluid F1-5a via optical means through viewing ports 12. In one embodiment, the sample analysis device 33 is capable of discerning multiple characteristics and properties of sample fluid F1-5a such as the quantity, size, shape, material characteristics, and type of particulate matter in sample fluid F1-5a. Sample analysis device 33 may also be equipped to generate images of the sample, enable real-time sample analysis and may be capable of analyzing both magnetic/ferromagnetic and non-magnetic/ferromagnetic particles. The sample analysis device may be an optical analysis device, particle counter, fluid analyzer, Fluid Sampler Utilizing Optical Near-Field Imaging as described in U.S. Pat. No. 5,572,320, incorporated by reference herein, conventional particle analyzer or any combination thereof. Preferably, the sample analysis device 33 is also capable of wirelessly transmitting the fluid sample analysis to a remotely located receiver.

After passing through viewing ports 12, fluid sample F1-5a enters chamber 15 through check valve 13. Fluid sample F1-5a may then be expelled through check valve 14 and into return conduit 18 by an upward motion of piston 16, which induces check valve 14 to open and ensures that check valve 13 remains closed. This expels the fluid sample F1-5a from chamber 15 into return conduit 18 whereby it is returned to the original fluid flow F1-5. The force required to actuate spring or ball of check valve 14 can be set such that the fluid pressure exerted by upward movement of piston 16 is sufficient to open valve 14. Ideally, this force may be set to optimize the expulsion of fluid sample F1-5a from chamber 15 into return conduit 18 and return of fluid sample F1-5a into flow tube 8. Preferably, the pressure induced by piston 16 and check valve 14 is significantly greater than the pressure in tube 8 so as to quickly force fluid sample F1-5a out of chamber 15 and into tube 8. In an exemplary embodiment, the pressure is preferably about ½ to about 5 times greater than the pressure in tube 8, more preferably, about 1 to about 5 times greater than the pressure in tube 8 and most preferably, about 1½ to about 5 times greater than the pressure in tube 8 in order to ensure that the returned sample can be forced back into pressurized flow F1-5 in tube 8. The more quickly fluid sample F1-5a is ejected from the fluid sampling system, the more quickly and efficiently other fluid samples may be collected and analyzed by the fluid sampling system.

Figure 2:
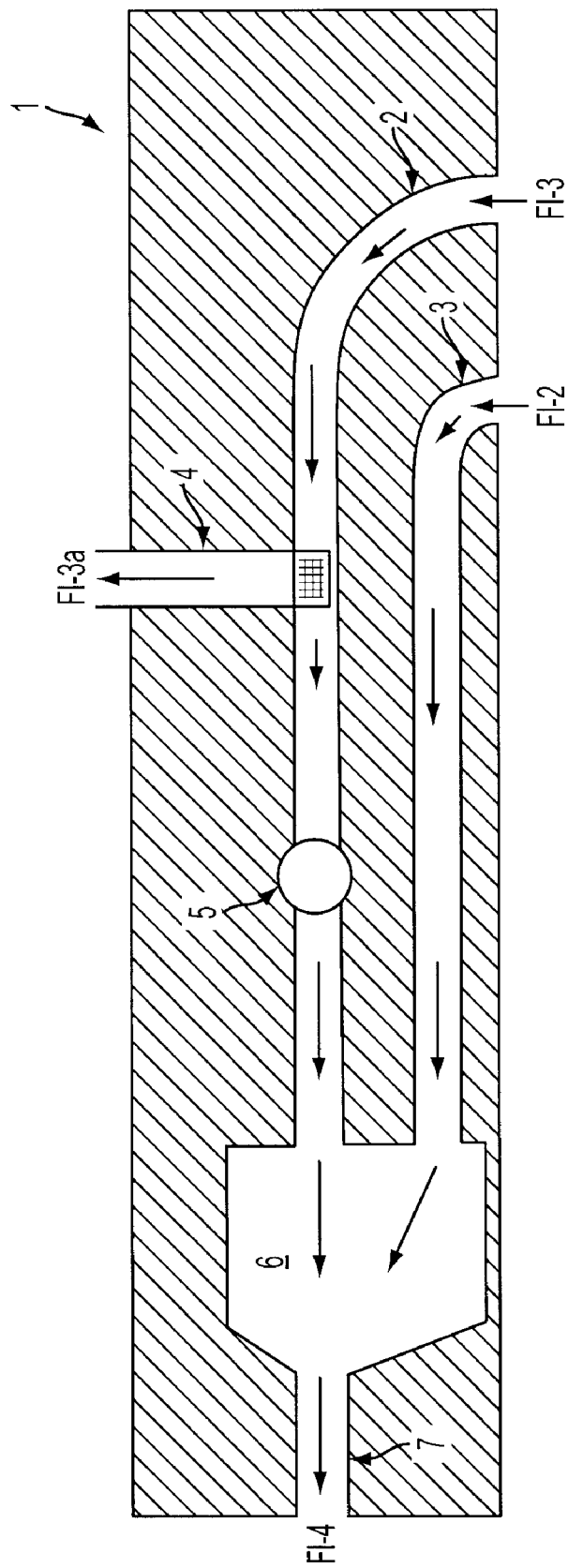
FIG. 2 is a schematic diagram of another embodiment of a fluid sampling system of the present invention that incorporates a means for obtaining deaerated fluid samples.

Fluid flow F1-5 in flow tube 8 may exhibit any of a variety of flow conditions. For example, in one embodiment, fluid flow F1-5 is an aerated fluid. For sample analysis, it may be desirable to thus de-aerate fluid flow F1-5 prior to passing a sample F1-5a along viewing ports 12. Fluid flow F1-5 may be a de-aerated, separated partial flow generated by a suitable de-aeration device. An example of a system for producing a de-aerated flow is shown in FIG. 2. An aerated flow is divided into a de-aerated flow F1-3 in channel 2 of system 1 and a gaseous component F1-2 of channel 3 of system 1. Sample F1-3a is extracted as de-aerated flow F1-3 passes sample extractor 4. The de-aeration system of FIG. 2 may optionally include a viewing port 5. The separated liquid and gaseous components F1-2 and F1-3 are recombined in chamber 6 as component F1-4 and passed back to flow tube 8 via a return conduit 7. This operation may be combined with the present invention and it may be combined with a full flow large particle detection device as described in U.S. Pat. No. 6,049,381, which is incorporated by reference herein.

Figure 3:
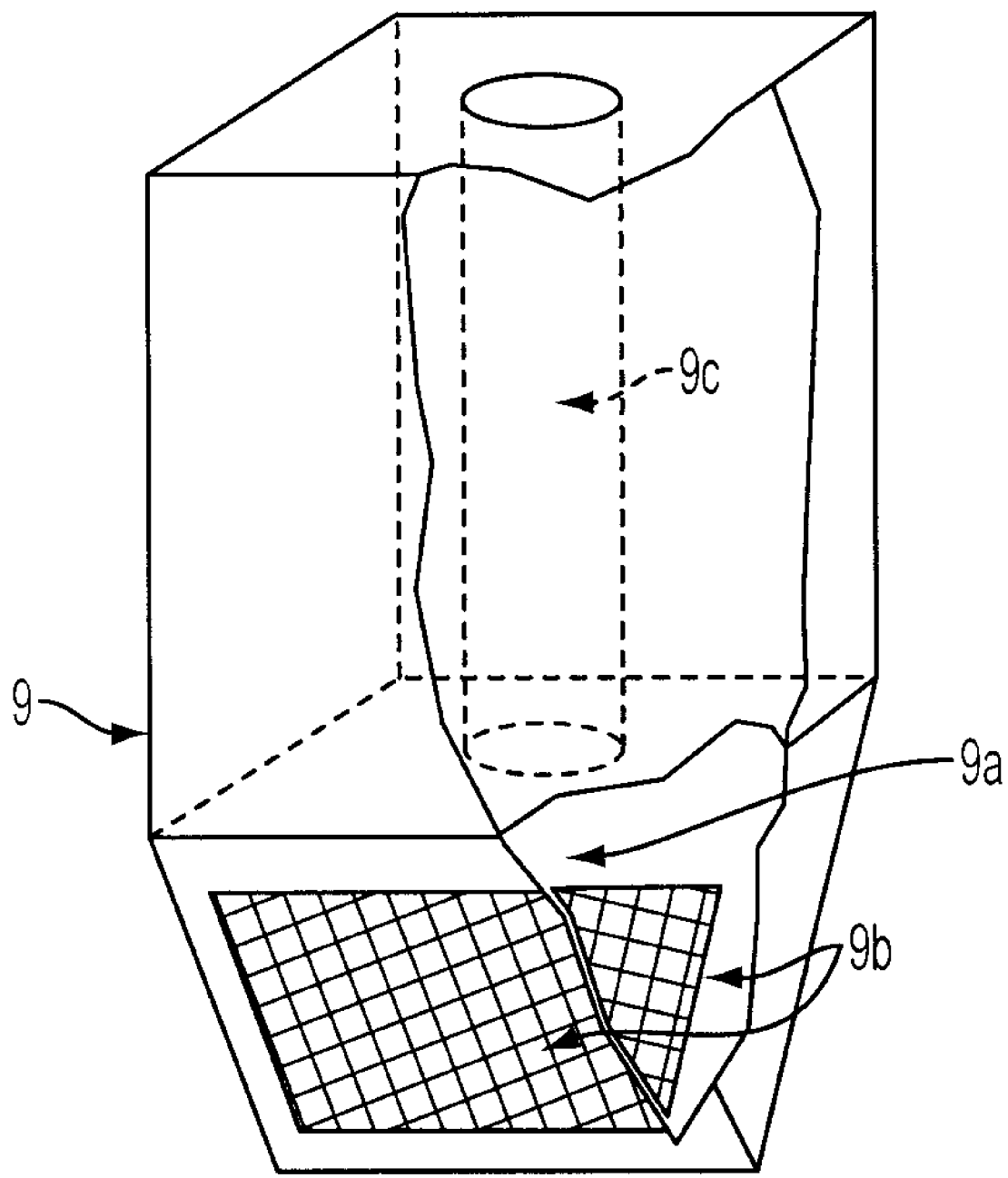
FIG. 3 is a partial cutaway view of an embodiment of a sample extractor in accordance with the present invention.

As fluid flow F1-5 passes sample extractor 9, fluid sample F1-5a may be extracted by suction, as described above. As shown in FIG. 3, sample extractor 9 may comprise a chamber 9a, which is connected to exit tube 9c and is at least partially surrounded by at least one filtration screen 9b. Filtration screen 9b may be, for example, a mesh like structure having multiple openings through which fluid flow F1-5 may pass. The dimensions of these openings may be varied by interchanging different filtration screens 9b in order to select the maximum size of the sample particulates which are to be allowed to pass through viewing gap 12a. The dimensions of the openings in screen 9b may be selected as desired. In a preferred embodiment, the dimensions of the openings are selected so as to provide particulate-entrained fluid samples having particulate sizes that are compatible with a particular sample analysis device 33. Preferably, the screen 9b allows sampling of particles of having particle sizes of from about 0.001 µm to about 200 µm, more preferably, from about 1 µm to about 150 µm, and most preferably, from about 1 µm to about 100 µm.

Preferably, at least 2 filtration screens 9b are provided within chamber 9a of sample extractor 9 so that they form an angle with respect to one another. In a preferred embodiment, one or multiple filtration screens 9b may be configured to form a "V" shape so as to efficiently channel the portion of the flow containing the particulate contaminants. The angled orientation of said filtration screens 9b enables extraction of fluid from at least two different directions, including a direction perpendicular to fluid flow F1-5.

In order to further optimize the process of sample extraction and obtain an accurate sample of fluid flow F1-5, sample extractor 9 is preferably oriented within flow tube 8 such that flow chamber 9c is located at the center of fluid flow F1-5. Since the coefficient of drag around the circumference of the flow tube 8 is greater than at the center of the fluid flow, fluid flow F1-5 may have a parabolic shape, wherein the flow is fastest at the center of the fluid flow. Contaminants and entrained particles are primarily swept along this central portion of the fluid flow. Also, flow chamber 9c is preferably located at the center of the fluid flow such that fluid flow F1-5 is parallel to a plane of filtration screen 9b. After fluid sample F1-5a is extracted from fluid flow F1-5 and passed through chamber 9a, the sample travels through exit tube 9c and into sample conduit 11.

Figure 4:
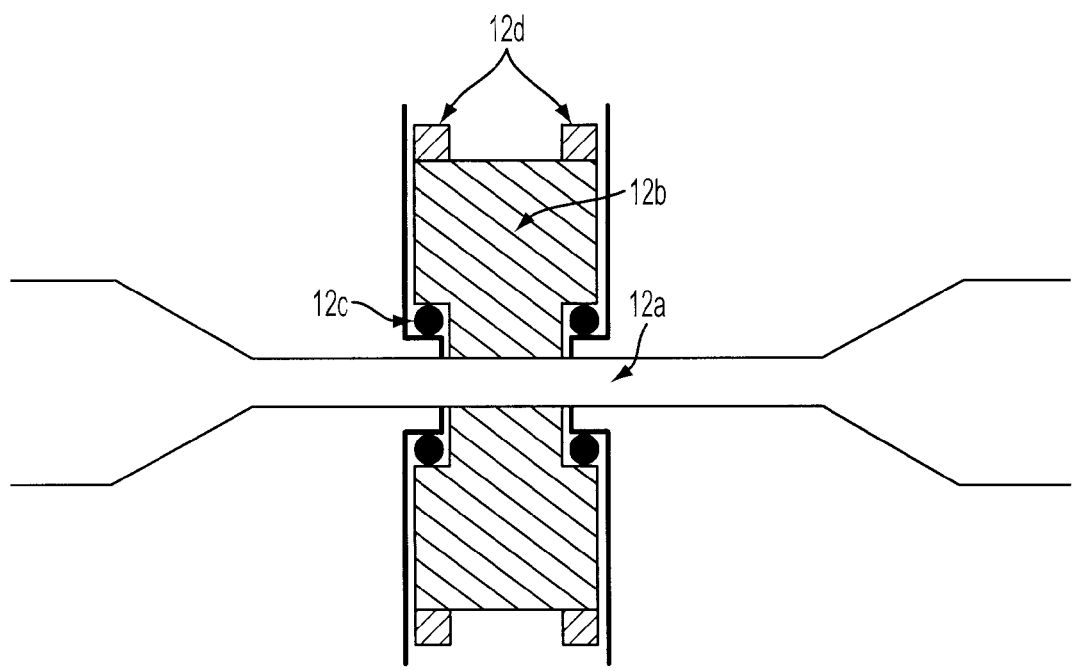
FIG. 4 is a cross-sectional view of an embodiment of a viewing port in accordance with the present invention.

Viewing ports 12 are shown in greater detail in FIG. 4. A viewing window 12b is securely set within sample conduit 11 at a location of a viewing gap 12a, using a resilient seal 12c and a compression nut 12d. The width of viewing gap 12a may be adjusted by the user and controlled by a suitable apparatus such as a set of shims (not shown), which can be used to separate windows 12b by a set distance that may be adjusted by the user. The separation between windows 12b may also be controlled by other conventional or suitable methods. Viewing windows 12b are adjusted so that gap 12a meets the design requirements of any desired sample analysis device 33 that operably functions with the fluid sampling system of the present invention. Windows 12b may be constructed from any suitable conventional material that meets the requirements of the desired sample analysis device 33. Preferably, window 12b is transparent over the range of wavelengths necessary for sample analysis. In order to maintain the structural integrity of the viewing ports 12 and to achieve the aforementioned desired gap distance, compression nut 12d compresses window 12b against resilient seal 12c such that window 12b becomes flush with the surface of viewing gap 12a.

The present invention is capable of operating with a wide range of flow conditions, including a variety of flow rates, pressures, volumes and temperatures. In an exemplary embodiment, fluid flow F1-5 may have a flow rate of about less than or equal to 1 liter/minute for some hydraulic applications. For some machinery lubricating oil systems, the flow rate may be about 2 liters/minute to about 80 liters/minute. Flow speeds depend on tube diameter and may vary form 0.01 meter/sec for some hydraulic applications to more than 20 meters/sec for some machinery lubrication systems. Sample extractor 9 is designed to accommodate any flow rate and extract a representative sample from the flow for analysis. The flow may be characterized as a laminar, transitional or turbulent flow. In an exemplary embodiment, the pressure of fluid flow F1-5 in tube 8 may vary from about 20 psi to about 3500 psi. In another exemplary embodiment, the invention is particularly suitable for hydraulic systems having high pressure flows from about 1000 psi to about 3500 psi, more preferably from about 1500 psi to about 2000 psi. In another exemplary embodiment, the invention is also suitable for lubricating oil systems having a low pressure flow from about 20 psi to about 100 psi. Furthermore, the fluid sampling system of the present invention is capable of isothermal operation with any flow volume and is capable of operating with fluid flows of any temperature, including extremely high temperatures.

Figure 5:
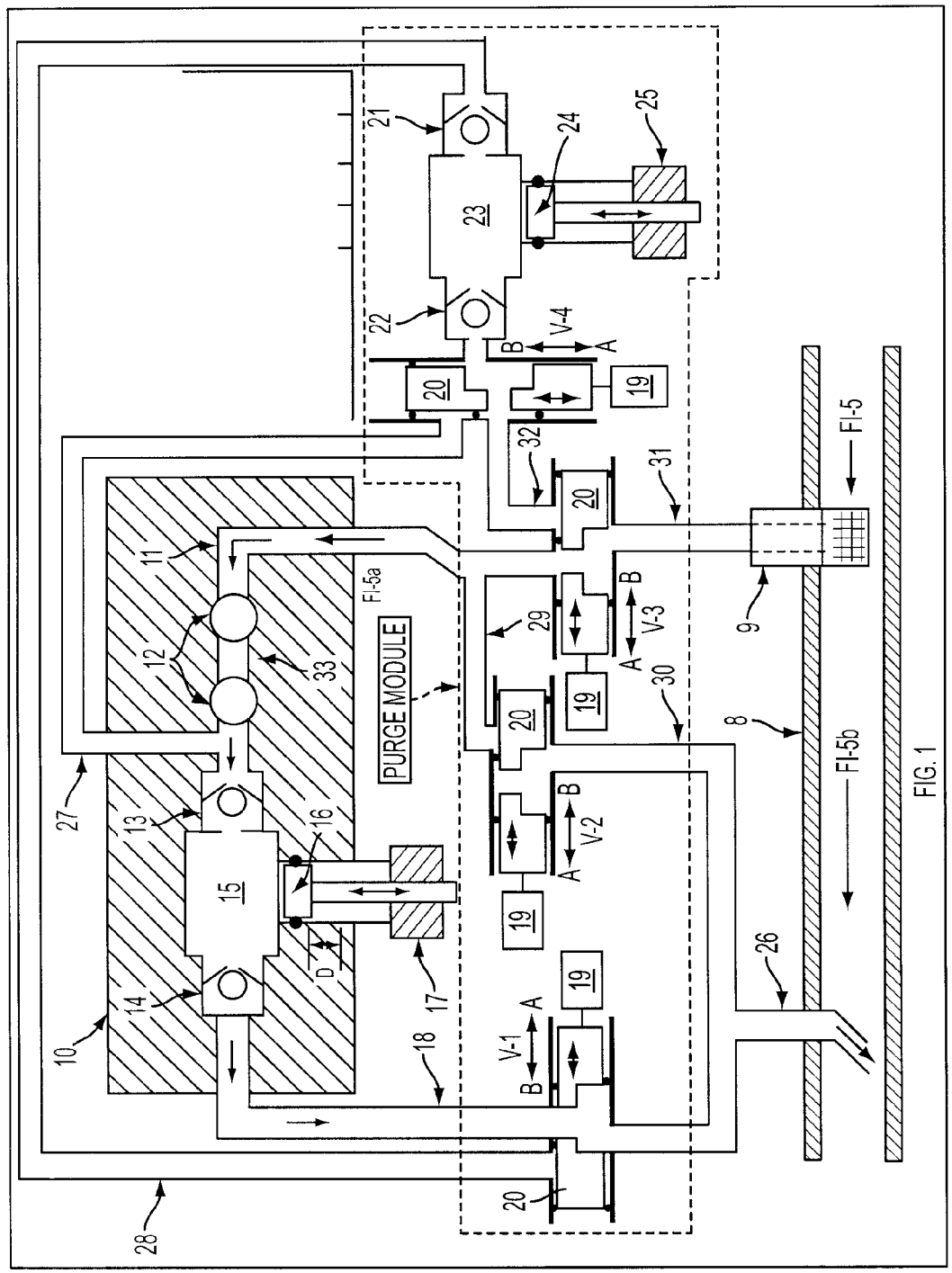
FIG. 5 is a schematic diagram of an alternative embodiment of the present invention showing a fluid sampling system including three fluid flow circuits and three operational modes: a sampling mode, a first purging mode and a second purging mode.
Figure 6A:
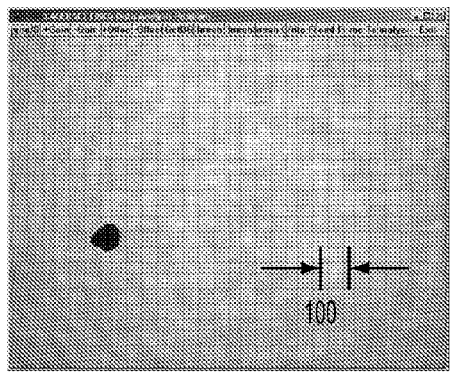
FIG. 6(a) is an image of a particle obtained using the fluid sampling system of Example 1.
Figure 6B:
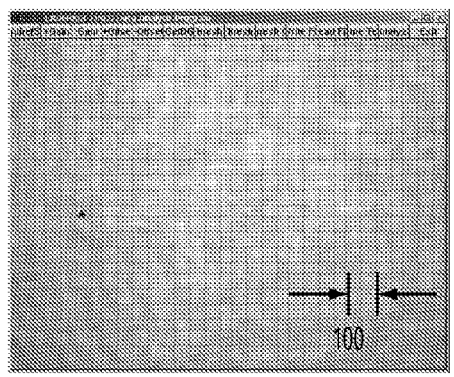
FIG. 6(b) is another image of a particle obtained using the fluid sampling system of Example 1.
Figure 6C:
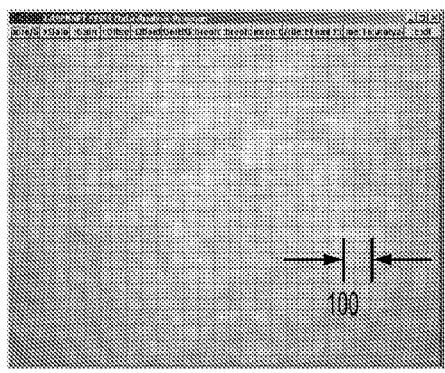
FIG. 6(c) is another image of a particle obtained using the fluid sampling system of Example 1.
Figure 6D:
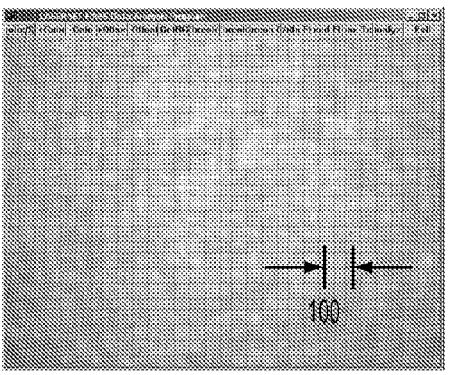
FIG. 6(d) is another image of a particle obtained using the fluid sampling system of Example 1.

As shown in FIG. 5, another embodiment of the present invention may include a fluid sampling system comprising at least two fluid flow circuits that enable the system to function in at least two different operational modes: a sampling mode, and a purging mode. The dotted lines shown in FIG. 5 outline the portion of the schematic that operates to carry out the purging mode. The different operational modes may be governed by the position of spooling valves V1-V4, as shown in Table 1. The operational modes of the present invention may be accomplished by using a single spool valve, a multiple spool valve arrangement, an arrangement involving individual valves with actuation means 19, or by any other suitable means that enables fluid sampling and purging. These valves may be remotely controlled and programmed so as to be positioned to operatively sample or purge.

TABLE 1

Valve Positions Relative to the 3 Operational Modes of the Present Invention

| Mode | Position of Valve V-1 | Position of Valve V-2 | Position of Valve V-3 | Position of Valve V-4 |
| --- | --- | --- | --- | --- |
| Sampling Mode | A | A | A | A |
| First Purging Mode (Sample Extractor 9) | B | A | B | A |
| Second Purging Mode (Viewing Port 12) | B | B | B | B |

Each of Valves V1-V4 operatively open one passageway and close another, thereby allowing flow to be diverted by the valve to the desired flow passage. As described above and as shown in FIG. 5, when valves V1-V4 are oriented in the A position so as to each selectively block one of at least two fluid flow pathways at each valve, the system enables fluid sampling via a first flow circuit. Each valve V1-V4 includes components 19 and 20 which enable valves V1-V4 to selectively block or open a particular fluid flow passage.

A second fluid flow circuit may be used to expel contaminants from all or a portion of the fluid sampling system by operating the system in purge mode. The purge mode is designed to remove, in part, any unwanted material that may have accumulated at various locations in the first flow circuit. For example, purge mode may be employed to remove unwanted materials from screens 9b of sample extractor 9 or from surfaces of viewing ports 12. When valves V-1 and V-3 are oriented in the B position and valves V-2 and V-4 are oriented in the A position, fluid may be drawn from flow tube 8 through first purge conduit 26, valve V-1, second purge conduit 28, spring loaded check valve 21 and into chamber 23, which, taken together, form a second flow circuit. The flow rate, volume, and pressure of fluid flow through the second fluid flow circuit may be regulated and/or induced by actuator 25, piston 24 and check valves 21 and 22 in the same manner of operation as described above for actuator 17, piston 16 and check valves 13 and 14 and the same types of apparatus may be employed for these parts. After reaching chamber 23, an upward motion of piston 24 ejects the fluid flow through check valve 22, valve V-4, third purge conduit 32, valve V-3, fourth purge conduit 31 and, finally, through sample extractor 9 before being expelled back into fluid flow F1-5. This reverse flow purges material build-up on the exterior of filtration screens 9b and furthermore functions to clean the second flow circuit and a portion of the first flow circuit as well.

A third fluid flow circuit may be used to expel contaminants from another portion of the fluid sampling system of the present invention by operating in a second purging mode. This second purging mode is designed to remove, in part, any unwanted material that may have accumulated on viewing ports 12. When valves V-1-V-4 are oriented in the B position, fluid may be drawn from flow tube 8 through first purge conduit 26, valve V-1, second purge conduit 28, check valve 21 and into chamber 23. As discussed above, the flow rate, volume, and pressure of fluid flow through the third fluid flow circuit may be regulated and/or induced by actuator 25, piston 24 and check valves 21 and 22 in the same manner in which actuator 17, piston 16 and check valves 13 and 14 operate. After reaching chamber 23, an upward motion of piston 24 ejects the fluid flow past check valve 22, through valve V-4 and into fifth purge conduit 27. The fluid is blocked from flowing into or through chamber 15 and return conduit 18 by valve V-1. Instead, the fluid is forced in a reverse direction through sample conduit 11 purging material build-up in and around viewing ports 12. The fluid is then forced through sample conduit 11, valve V-2, sixth purge conduit 30 and first purge conduit 26 before returning to flow tube 8. In addition to cleaning the area surrounding viewing ports 12, this second purging mode enables cleaning of a portion of sample conduit 11.

The present invention provides an advantageous method and system for fluid sampling because it utilizes a flexible mechanism including an adjustable reciprocating piston and two check valves to induce and/or regulate fluid extraction and eject a fluid sample, so as to be operable with a high pressure and/or high flow rate fluid flow system. The present invention is capable of controlling and optimizing the process of fluid sampling over a wide range of flow pressures, flow rates, flow volumes and temperatures; therefore, it provides a more efficient and reliable system. Additionally, the invention minimizes the possibility of fluid leaks throughout the fluid sampling system. The fluid sampling system of the present invention is also advantageous in that it may be portable, enables real-time sample analysis, and is capable of analyzing both magnetic/ferromagnetic and non-magnetic/ferromagnetic particles, capable of operating in both a sampling and a purging mode and utilizes a novel sample extractor capable of optimizing fluid extraction and obtaining a sample representative of the fluid flow. For example, the sampling system can be implemented in a device that fits within a space of 25 by 25 cm, if desired.

The method of the present invention, described above, has a number of applications and may be particularly applicable for analyzing fluid samples from hydraulic and lubricating systems. It is envisioned that the invention may be particularly useful for monitoring fluids in various machinery such as oil-wetted machinery, earth-moving equipment, machine-tools, motors, generators, engines and rotating machines such as gears, bearing systems, hydraulic and lubrication systems on land vehicles, shipboard machinery, rotary wing and fixed wing aircraft and industrial and process machinery of all types.

EXAMPLE

A working model of a portable fluid sampling system of the present invention was built, having a total length of about 25-30 cm. As described above, the system comprises a sample extractor 9, viewing ports 12, sample analysis device 33, actuator 24 and piston 25.

Figure 7A:
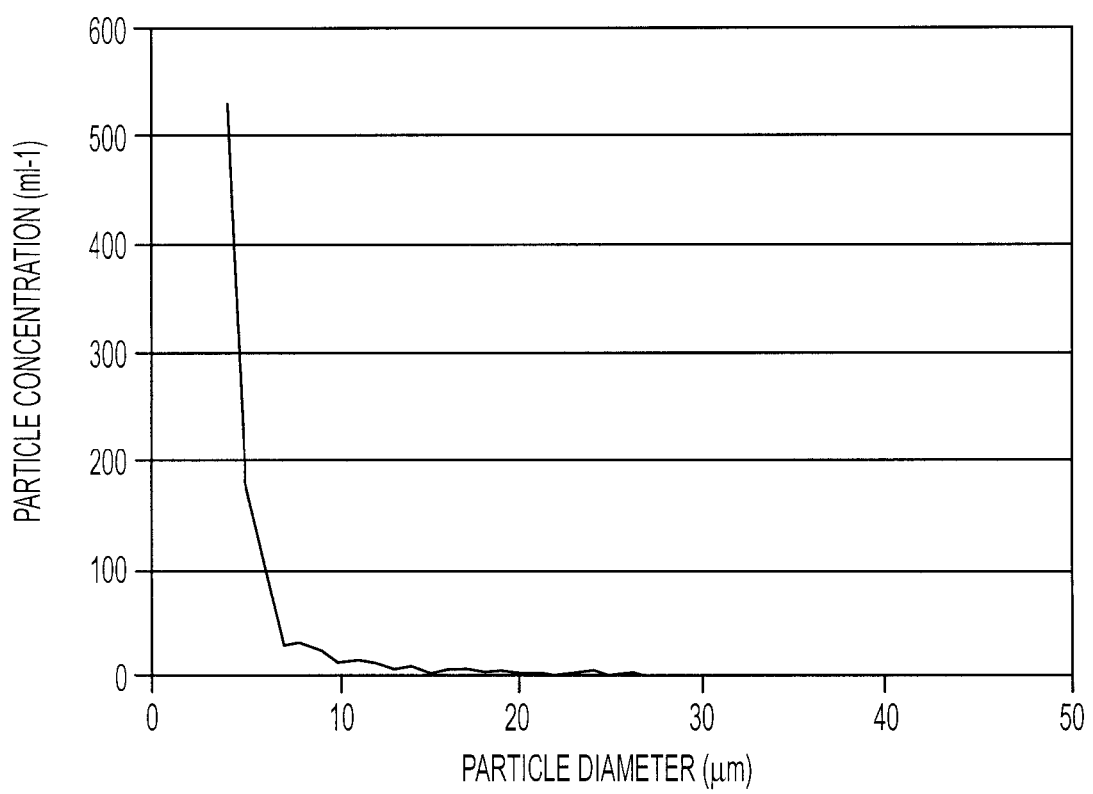
FIG. 7(a) is a graph of particle concentration as a function of particle size showing the size distribution of the particles of one fluid sample.
Figure 7B:
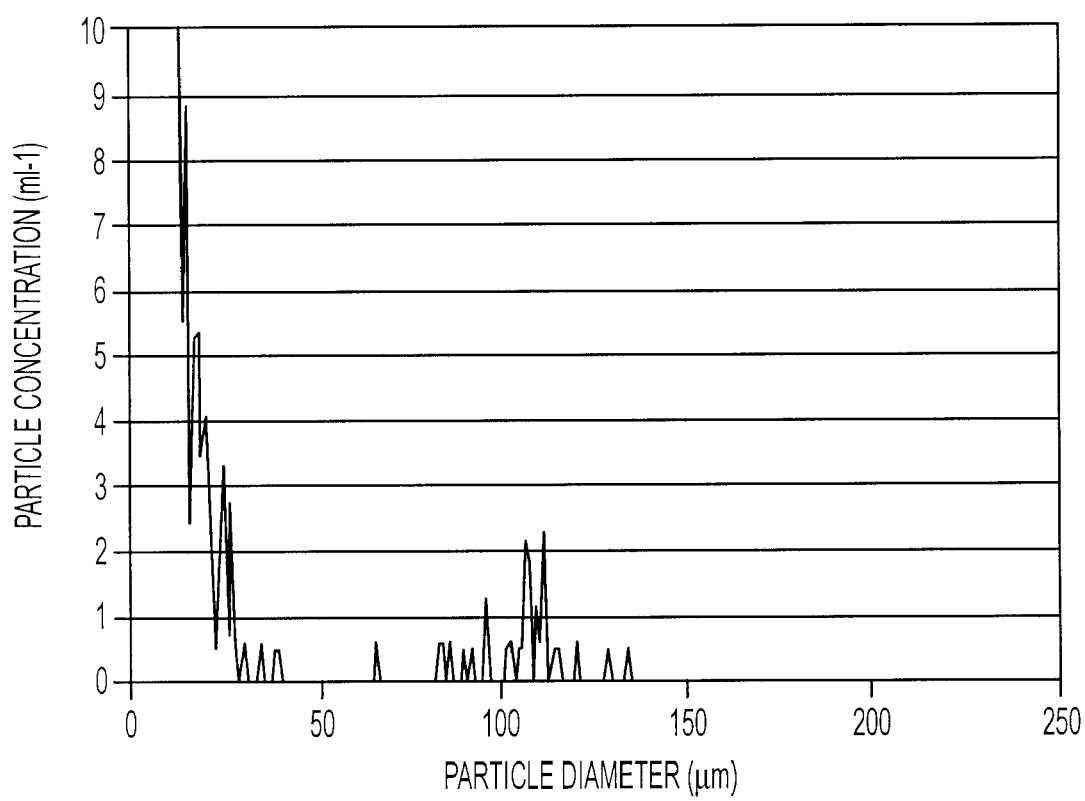
FIG. 7(b) is a graph of particle concentration as a function of particle size showing the particle concentration distribution of FIG. 7(a).

The fluid sampling system was used to obtain and optically test particle entrained samples from a high pressure fluid flow system. The samples were analyzed using a LaserNet Fines device produced by Lockheed Martin. The particle size distributions shown in FIG. 7(a) were obtained by the analysis of several thousand image frames such as shown in an enlargement of FIGS. 6(a)-6(d), from several thousand fluid sample draws from the fluid sampling system. FIG. 7(b) is an enlargement of FIG. 7(a) showing that particles as large as 100 μm are sampled from the system. These images demonstrate that the fluid sampling system may be used to capture particulates on the order of several microns to about 100 microns.

Having described the preferred embodiments of the invention which are intended to be illustrative and not limiting, it is noted that modifications and variations can be made by persons skilled in the art in light of the above teachings. It is therefore to be understood that changes may be made in the particular embodiments of the invention disclosed which are within the scope and spirit of the invention as outlined by the appended claims. Having thus described the invention with the details and particularity required by the patent laws, the intended scope of protection is set forth in the appended claims.

The invention claimed is:

1. A fluid sampling system for extracting and analyzing a sample of fluid from a fluid flow system, said fluid sampling system comprising:
   a. a sample extractor;
   b. a sample conduit fluidly connected to said sample extractor and provided with a sample analysis device;
   c. a pressure intensifier operatively connected to said sample conduit for exerting pressure or suction on a fluid located in said sample conduit;
   d. two valves positioned in said sample conduit, one on either side of said pressure intensifier, said valves arranged such that pressure or suction exerted by said pressure intensifier simultaneously causes one said valve to be open and another said valve to be closed such that said pressure intensifier and said valves are capable of adjustably regulating flow of a fluid sample in said fluid sampling system.

2. The fluid sampling system of claim 1, adapted for sampling from a fluid flow having a pressure of from about 100 psi to about 2000 psi.

3. The fluid sampling system of claim 1, adapted for sampling from a fluid flow having a pressure of from about 1500 psi to about 2000 psi.

4. The fluid sampling system of claim 1, wherein said sample extractor comprises at least one filtration screen having substantially a V shape and wherein said filtration screen is oriented such that the plane of said filtration screen is parallel to a fluid flow within said fluid flow system.

5. The fluid sampling system of claim 1, wherein said pressure intensifier is a piston.

6. The fluid sampling system of claim 1, wherein said system is capable of regulating suction such that a suction pressure exerted on a sample fluid located within fluid sampling system is about 1 to about 1½ times a pressure of a fluid in said fluid flow system.

7. The fluid sampling system of claim 1, wherein said system is capable of expelling a fluid sample from said fluid sampling system with a pressure of about 1½ to about 5 times of a pressure of a fluid in said fluid flow system.

8. The fluid sampling system of claim 1, wherein said valves are check valves selected from the group consisting of: a spring loaded check valve and a ball valve.

9. The fluid sampling system of claim 1, further comprising a second pressure initiator and a second fluid conduit operatively connected to the fluid sampling system to permit purging of at least a portion of said fluid sampling system.

10. The fluid sampling system of claim 9, wherein said system further comprises at least one viewing port and wherein said purged portion of said fluid sampling system comprises said viewing port.

11. The fluid sampling system of claim 9, wherein said purged portion of said fluid sampling system comprises said sample extractor.

12. The fluid sampling system of claim 9, further comprising one or more valves to enable said fluid sampling system to be switched from a fluid sampling mode to a fluid purging mode.

13. The system of claim 12, wherein said valves are spooling valves.

14. The system of claim 1, further comprising:
a fluid return conduit operably coupled to the sample conduit and to said fluid flow system, configured to return said fluid sample to said fluid flow system.

15. The system of claim 14, wherein said sample extractor has a fluid chamber positioned in the center of a fluid flow in the fluid flow system, and at least one filtration screen having a plane oriented parallel to the fluid flow within said fluid flow system.

16. The system of claim 1, further comprising:
a viewing port;
an optical analysis device positioned to analyze a fluid flow passing by the viewing port; and
a deaerator arranged to deaerate the fluid sample before the sample passes the viewing port.

17. The system according to claim 16, further comprising:
a chamber coupled to a conduit carrying the deaerated fluid sample and coupled to a conduit carrying a gaseous component produced by the deaerator system, said chamber configured to recombine said deaerated fluid sample and said gaseous component and pass the recombined fluid sample to the fluid return conduit.

* * * * *